United States Patent [19]

Zaiger et al.

[11] Patent Number: Plant 6,763

[45] Date of Patent: Apr. 25, 1989

[54] INTERSPECIFIC TREE (FLAVOR SUPREME)

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 135,155

[22] Filed: Dec. 18, 1987

[51] Int. Cl.[4] ..... A01H 5/03

[52] U.S. Cl. ..... Plt./38

[58] Field of Search ..... Plt./38-39

*Primary Examiner*—Robert E. Bagwill

[57] ABSTRACT

This new distinct variety relates to an interspecific (plum×plumcot) tree which has the following unique combination of desirable features:

1. Production of fruit with excellent flavor and eating quality.
2. Firm flesh texture of fruit, intermediate between plum and apricot.
3. Fruit with high brix (soluble solids) average 17%.
4. Heavy and regular production.
5. Vigorous, semi-upright growth.
6. Good shipping and storage quality of fruit.

1 Drawing Sheet

ORIGIN OF THE VARIETY

The present variety of interspecific (plum×plumcot) tree was originated by us in the experimental orchard located at Modesto, Calif. as a first generation seedling from a cross between a plum selection identified as 5G1230 and a plumcot selection identified as 4G1180. Both of the above parents were selected from a group of open pollinated Red Beaut Plum (U.S. Plant Pat. No. 2,539) seedlings grown in our experimental orchard.

ASEXUAL REPRODUCTION OF THE VARIETY

The present variety of interspecific tree was asexually reproduced by budding and grafting, as performed by us in the experimental orchard located at Modesto, Calif., shows that all characteristics run true to form and are established and transmitted through succeeding propagations.

SUMMARY OF THE VARIETY

The present variety of interspecific (plum×plumcot) tree which is of large size, dense, semi-upright in growth and a regular and productive bearer of medium size, clingstone fruit. The fruit is further characterized by having firm flesh texture which is intermediate between plum and apricot, being excellent in flavor and eating quality, and having good storage and shipping quality.

DESCRIPTION OF THE PHOTOGRAPHS

The accompanying color photographs show typical specimens of the fruit and foliage of the new variety, with the upper and lower surface of the leaves being illustrated and the exterior and a cross sectional view of the fruit divided in the suture plane to reveal flesh coloration and showing a stone remaining in place. The illustrations were taken shortly after being picked at maturity (firm ripe) and the colors are as nearly true as is reasonably possible in a color representation of this type.

DESCRIPTION OF THE VARIETY

The following is a botanical description of the present new and distinct variety of interspecific (plum×plumcot) tree, its foliage and fruit as based on observations of specimens grown at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Semi-upright.
- *Density.*—Dense.
- *Production.*—Productive.
- *Bearing.*—Regular.

Trunk:
- *Size.*—Medium to large.
- *Surface.*—Shaggy.
- *Color.*—Brown to grayish brown.

Branches:
- *Size.*—Medium.
- *Surface.*—Medium rough.
- *Lenticels.*—Medium number. Medium to large size.
- *Color.*—Brown to dark brown.

Leaves:
- *Size.*—Large. Average length — $4\frac{3}{4}''$ to $5''$. Average width — $1\frac{7}{8}''$ to $2\frac{1}{8}''$.
- *Form.*—Oblanceolate.
- *Margin.*—Finely serrate.
- *Texture.*—Smooth.
- *Petiole.*—Average length — $1\frac{1}{8}''$. Average thickness — $1/16''$.
- *Glands.*—Globose. Number varies 1 to 4. Average number 2. Usually located on lower portion of leaf blade, with only a few located on upper portion of petiole.
- *Color.*—Upper surface — green to dark green (27-F-6) to (27-F-8). Lower surface — green to dull green (28-E-6) to (28-E-8).

Flower buds:
- *Size.*—Medium.
- *Form.*—Plump — free.

Flowers:
- *Blooming period.*—First Bloom — Mar. 1, 1987. Full Bloom — Mar. 4, 1987. Varies slightly with climatic conditions.
- *Size.*—Medium.
- *Color.*—White.

*Pistil pubescents.*—Wanting.
*Pollen.*—Present.

Fruit:
*Maturity when described.*—Firm ripe.
*Date of first picking.*—June 13, 1987.
*Date of last picking.*—June 20, 1987.
*Size.*—Medium. Average diameter axially 2" to 2¼". Average transversely in suture plane 2⅛" to 2¼".
*Form.*—Globose to slightly flattened on stem end.
*Suture.*—Shallow. Nearly smooth. Extends from base to apex.
*Base.*—Retuse.
*Apex.*—Rounded to very slight point.
*Cavity.*—Rounded to slightly elongated in suture plane. Average depth — ⅜". Average breadth — ½".

Skin:
*Thickness.*—Medium.
*Texture.*—Medium.
*Tendency to crack.*—None.
*Down.*—Wanting.
*Bloom.*—Moderate to heavy.
*Color.*—Violet brown to purplish gray (11-F-2) to (12-F-3). Mottled with small lighter colored dots randomly spaced.

Flesh:
*Texture.*—Firm, but delicate. Intermediate between plum and apricot.
*Ripens.*—Fairly uniform, slightly later at stem end.
*Amygdlin.*—Undetected.
*Juice.*—Moderate.
*Flavor.*—Excellent. Sweet — delicate balance between acid and sugar.
*Fibers.*—Few. Tender.
*Eating quality.*—Excellent.

*Color.*—Deep red to bordeaux (11-C-8) to (11-D-8). Slightly lighter color near stem cavity. Pit cavity — dark red (11-E-3).

Stone:
*Type.*—Clingstone.
*Size.*—Medium. Average length — 15/16'. Average breadth — 11/16". Average thickness — 5/16".
*Form.*—Ovid.
*Surface.*—Regularly pitted, only slightly throughout. Ridges near base with ridges extending across the surface on both sides of suture plane.
*Side.*—Unequal to equal.
*Base.*—Rounded to straight.
*Apex.*—Acuminate.
*Tendency to split.*—None.
*Color.*—Reddish brown (9-D-8) to (9-E-8).

Use: Dessert.
*Market.*—Local and long distance.
Keeping quality: Good.
Shipping quality: Good.

The interspecific (plum×plumcot) tree and its fruit herein described may vary in slight detail due to climatic, soil conditions and cultural practices under which the variety may be grown; the present description being of the variety grown under the ecological conditions prevailing at Modesto, Calif.

We claim:

1. A new and distinct variety of interspecific (plum×plumcot) tree, substantially as illustrated and described, characterized by its large size, being vigorous, semi-upright in growth and being a regular and productive bearer of medium size, firm, red flesh, clingstone fruit, with excellent flavor and eating quality and the ability to ship to long distance markets.

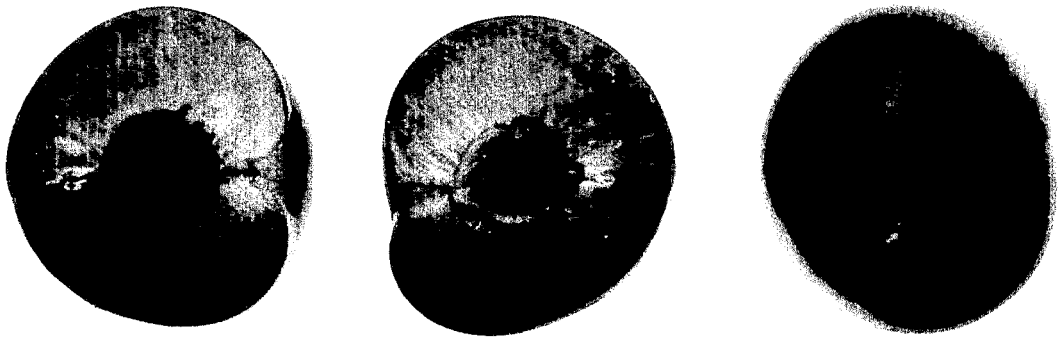
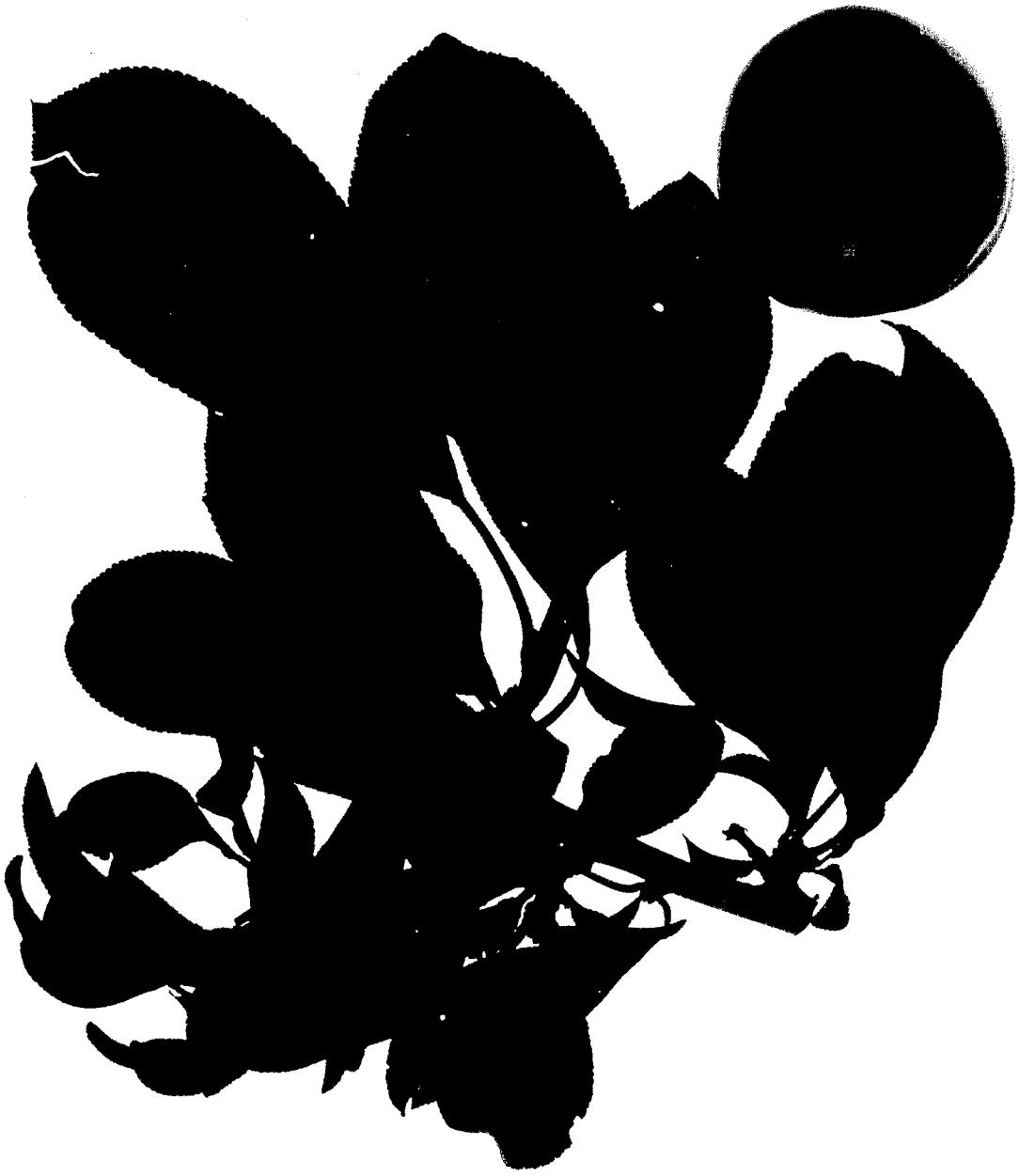

* * * * *